US010537686B2

(12) United States Patent
Mirabito et al.

(10) Patent No.: US 10,537,686 B2
(45) Date of Patent: *Jan. 21, 2020

(54) APPARATUS AND METHOD FOR THE PREPARATION AND ADMINISTRATION OF BLOOD COMPONENTS

(71) Applicants: HEALEON MEDICAL LTD., Tel-Aviv (IL); GENESIS BIOLOGICS HOLDINGS LTD., Tel-Aviv (IL)

(72) Inventors: A. Jason Mirabito, Derry, NH (US); Omer Peled, Haifa (IL); Shada Abu Hattum, Yaffa Nazareth (IL)

(73) Assignees: HEALEON MEDICAL LTD., Tel-Aviv (IL); GENESIS BIOLOGICS HOLDINGS LTD., Tel-Aviv (IL)

( * ) Notice: Subject to any disclaimer, the term of this patent is extended or adjusted under 35 U.S.C. 154(b) by 415 days.

This patent is subject to a terminal disclaimer.

(21) Appl. No.: 15/293,384

(22) Filed: Oct. 14, 2016

(65) Prior Publication Data
US 2017/0028137 A1    Feb. 2, 2017

Related U.S. Application Data

(63) Continuation of application No. PCT/US2015/026270, filed on Apr. 17, 2015.
(Continued)

(51) Int. Cl.
*A61M 5/00* (2006.01)
*A61M 5/315* (2006.01)
(Continued)

(52) U.S. Cl.
CPC ..... *A61M 5/31596* (2013.01); *A61B 18/1477* (2013.01); *A61B 18/203* (2013.01);
(Continued)

(58) Field of Classification Search
CPC .............. A61B 18/1477; A61B 18/203; A61B 2018/00005; A61B 2018/143;
(Continued)

(56) References Cited

U.S. PATENT DOCUMENTS 5,971,953 A    10/1999   Bachynsky
2006/0258977 A1   11/2006  Lee
(Continued)

FOREIGN PATENT DOCUMENTS

GB    2 443 799 A    5/2008
WO    2014001880    1/2014

OTHER PUBLICATIONS

Search Report—Corresponding PCT Application No. PCT/US2015/026270, dated Oct. 27, 2016, 6 pages.
EP, 15779231.8 Supplementary Search Report, dated Jan. 23, 2018.

*Primary Examiner* — Benjamin J Klein
(74) *Attorney, Agent, or Firm* — One LLP

(57) ABSTRACT

A dual chambered syringe includes: an inner barrel defining a first inner chamber, the inner barrel having an apertured stopper at its distal end, the inner barrel being open at its proximal end; a shaft adapted to fit within the inner barrel, the shaft having a distal end which is engageable with the aperture of the stopper; a device for controlling engaging and disengaging of the distal end of the shaft with the aperture of the stopper; an outer barrel concentric with the inner barrel defining a second inner chamber, the outer barrel having a distal end for receiving and dispensing fluids and a proximal end into which the distal end of the inner barrel is insertable into the second inner chamber; the apertured stopper engages the second inner chamber of the outer barrel and selectively prevents or permits the passage of fluids between the outer barrel second chamber and the inner barrel first chamber; the inner barrel having an engageable surface on its outside surface; and, the outer barrel having
(Continued)

operatively associated therewith an engaging device for selective engagement and disengagement with the engageable surface on the inner barrel.

22 Claims, 11 Drawing Sheets

Related U.S. Application Data

(60) Provisional application No. 61/980,612, filed on Apr. 17, 2014.

(51) Int. Cl.

| | | |
|---|---|---|
| *A61B 18/14* | (2006.01) | |
| *A61M 1/02* | (2006.01) | |
| *A61M 5/42* | (2006.01) | |
| *A61M 37/00* | (2006.01) | |
| *A61N 1/05* | (2006.01) | |
| *A61M 1/36* | (2006.01) | |
| *A61B 18/20* | (2006.01) | |
| *A61N 1/32* | (2006.01) | |
| *A61M 1/38* | (2006.01) | |
| *A61B 18/00* | (2006.01) | |

(52) U.S. Cl.
CPC .......... *A61M 1/029* (2013.01); *A61M 1/3693* (2013.01); *A61M 1/38* (2013.01); *A61M 5/31586* (2013.01); *A61M 5/425* (2013.01); *A61M 37/0015* (2013.01); *A61N 1/0502* (2013.01); *A61N 1/328* (2013.01); *A61B 2018/00005* (2013.01); *A61B 2018/00458* (2013.01); *A61B 2018/143* (2013.01); *A61B 2018/1467* (2013.01); *A61M 2005/31598* (2013.01); *A61M 2037/0023* (2013.01); *A61M 2037/0038* (2013.01)

(58) Field of Classification Search
CPC .......... A61B 2018/1467; A61M 1/029; A61M 1/3693; A61M 1/38; A61M 5/31586; A61M 5/31596; A61M 5/425; A61M 37/0015; A61M 2005/31598; A61M 2037/0023; A61M 2037/0038; A61N 1/328

See application file for complete search history.

(56) References Cited

U.S. PATENT DOCUMENTS

| | | |
|---|---|---|
| 2012/0065551 A1 | 3/2012 | Aviad et al. |
| 2013/0126559 A1 | 5/2013 | Cowan et al. |
| 2014/0121587 A1 | 5/2014 | Sallberg et al. |
| 2018/0264199 A1* | 9/2018 | Mirabito ............... A61M 1/029 |

\* cited by examiner

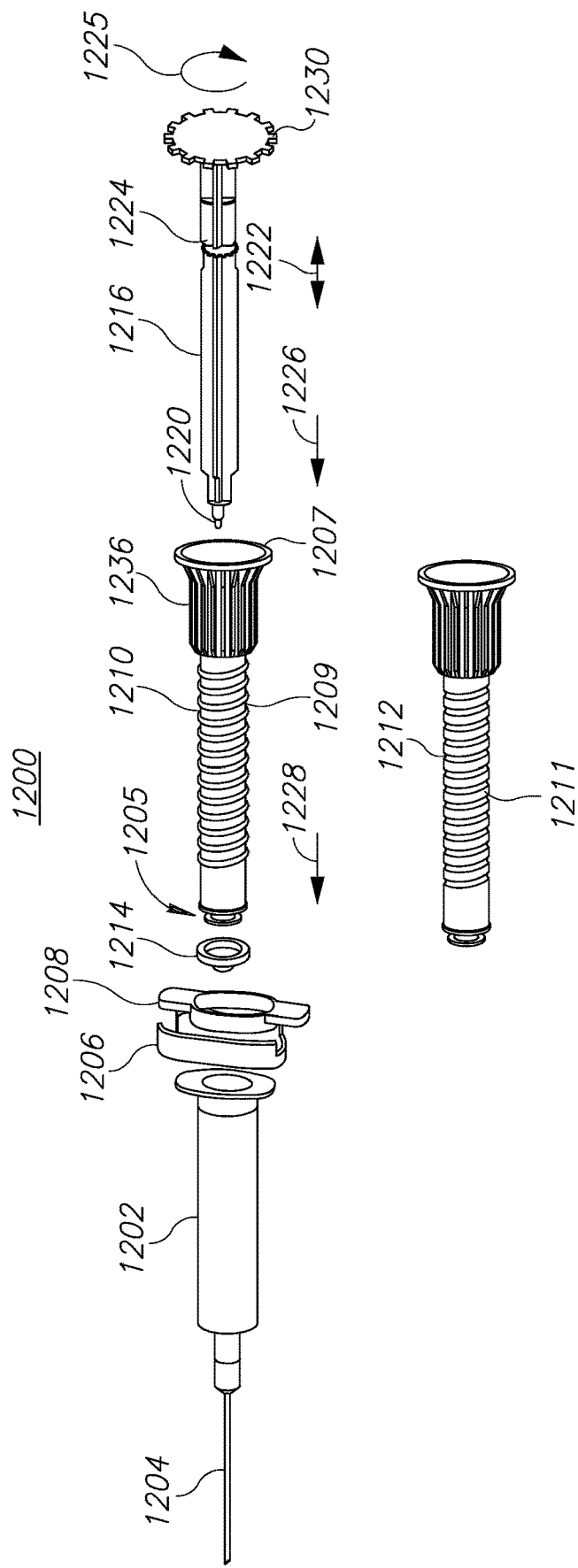
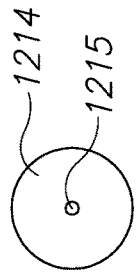
FIG.12C
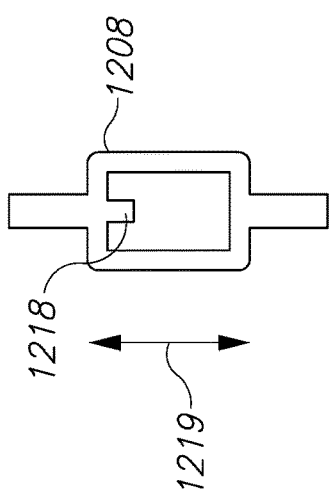
FIG.12B
FIG.12A

APPARATUS AND METHOD FOR THE PREPARATION AND ADMINISTRATION OF BLOOD COMPONENTS

CROSS REFERENCE TO RELATED APPLICATION

This application is a continuation application of PCT Application Serial No. PCT/US2015/26270, filed Apr. 17, 2015, which claims the benefit of priority to U.S. Provisional Patent Application No. 61/980,612, filed Apr. 17, 2014. The complete disclosures of these applications are hereby incorporated by reference herein.

FIELD OF THE INVENTION

The present invention relates to an apparatus and method for preparing platelets rich plasma (PRP) and delivering systems for one or more components to the human skin.

BACKGROUND OF THE INVENTION

Skin rejuvenation is occupying a significant part in the aesthetic field as it is deals with wrinkles, scars, pores, pigmentation and skin textures. Various materials, chemical and biological, are used for this purpose and a lot of delivery systems have been developed to assure an effective delivery to the different layers of the skin.

Recently, platelet rich plasma or PRP is proving to be efficient for skin rejuvenation procedures. Platelets contain several growth factors that are necessary to the healing and tissue renewal process. Many researches have presented results of PRP used for rejuvenation that was applied topically to the face or injected to the deeper skin layers. In addition, the PRP treatment was combined in several more researches with energy source treatments as ultrasound and fractional laser for improving outcomes and decreasing healing time.

The current methods for applying PRP are still not optimized to be the most efficient for each treatment. The efficiency of the treatment relies on the several aspects such as the amount of PRP used, the location of applying the PRP whether it is topical or in any of the skin layers, and it also depends on the diffusion of the PRP through the skin layers.

Fractional CO2 laser therapy is based on the theory of fractional photothermolysis. It has been used to treat skin problems, such as scar removal, skin tightening and skin rejuvenation. Two types of fractional laser treatments are available presently, nonablative and ablative. Nonablative fractional laser is less invasive, provides good clinical outcomes but is not sufficient to treat the above mentioned skin problems at a single treatment compared to an ablative laser treatment. The ablative fractional laser treatment creates ablative microscopic channels of thermal injury that causes skin tightening and smoothening. This effect is achieved by collagen remodeling that causes the skin to re-epithelialize. Despite its advantageous over nonablative laser, ablative laser has a longer down time and more adverse reactions for patients, such as erythema, acne, milia and infection. Hence, the aesthetic field has been concerned about improving the results of skin rejuvenation but shortening the recovery or downtime from the treatment. A few studies have suggested the use of PRP after fractional laser treatment. (Lee et al. The efficacy of autologous platelet rich plasma combined with ablative carbon dioxide fractional resurfacing for acne scars: a simultaneous split—face trial, Dermatol Surg, 2011) suggested faster healing occurs for the skin areas that have been treated with PRP after ablative fractional laser treatment for acne scars. Less Erythema was observed 4 days after the treatment and an improved overall clinical appearance of acne scaring occurred for PRP treated areas. (Gawdat et al., Autologous platelet rich plasma: topical versus intradermal after fractional ablative carbon dioxide laser treatment of atrophic acne scars, Dermatol Surg, 2014) compared improvement of acne scars after ablative fractional treatment when PRP was applied topically or injected intradermally. The same improvement in acne scaring reduction was showed for both application methods but significantly lower pain levels were shown for the topical application of PRP after fractional treatment. The above mentioned methods disclose applying PRP after fractional treatment is completed but yet no method has suggested to apply PRP into newly ablated channels have been formed by fractional treatment.

SUMMARY OF THE INVENTION

In an aspect, a dual chambered syringe includes an inner barrel defining a first inner chamber, in which the inner barrel has an apertured stopper at its distal end, the inner barrel being open at its proximal end; a shaft adapted to fit within the inner barrel, the shaft having a distal end which is engageable with the aperture of the stopper; it also includes a device for controlling engaging and disengaging of the distal end of the shaft with the aperture of the stopper; an outer barrel concentric with the inner barrel defines a second inner chamber, the outer barrel having a distal end for receiving and dispensing fluids and a proximal end into which the distal end of the inner barrel is insertable into the second inner chamber. The apertured stopper engages the second inner chamber of the outer barrel and selectively prevents or permits the passage of fluids between the outer barrel second chamber and the inner barrel first chamber; the inner barrel has an engageable surface on its outside surface; and, the outer barrel has operatively associated therewith an engaging device for selective engagement and disengagement with the engageable surface on the inner barrel.

In another aspect, in the dual chambered syringe, the engageable surface of the inner barrel is in the form of one of an internal screw thread or an external screw thread, and the engaging device engages the internal or external screw thread.

In yet another aspect, in the dual chambered syringe, the engaging device is a protrusion which is selectively engaged with or not engaged with the internal or external screw thread.

In another aspect, in the dual chambered syringe, the device for controlling engaging and disengaging of the shaft with the aperture of the stopper comprises corresponding internal and external screw threads on one of the outside of the shaft and the interior of the first inner chamber.

In yet a further aspect, in the dual chambered syringe, the inner barrel is movable in distal and proximal directions by pushing or pulling the inner barrel along the longitudinal axis of the outer barrel or by turning the inner barrel in either direction when the engaging device engages the inner barrel engageable surface.

In a further aspect, in the dual chambered syringe, the outer barrel distal end receives a dispensing apparatus, the dispensing apparatus dispensing fluids from the syringe on skin and tissue surface.

BRIEF DESCRIPTION OF THE DRAWINGS

FIGS. 12A, 12B and 12C illustrate a further embodiment of a dual chamber syringe.

DETAILED DESCRIPTION OF THE INVENTION

Figure 1A:
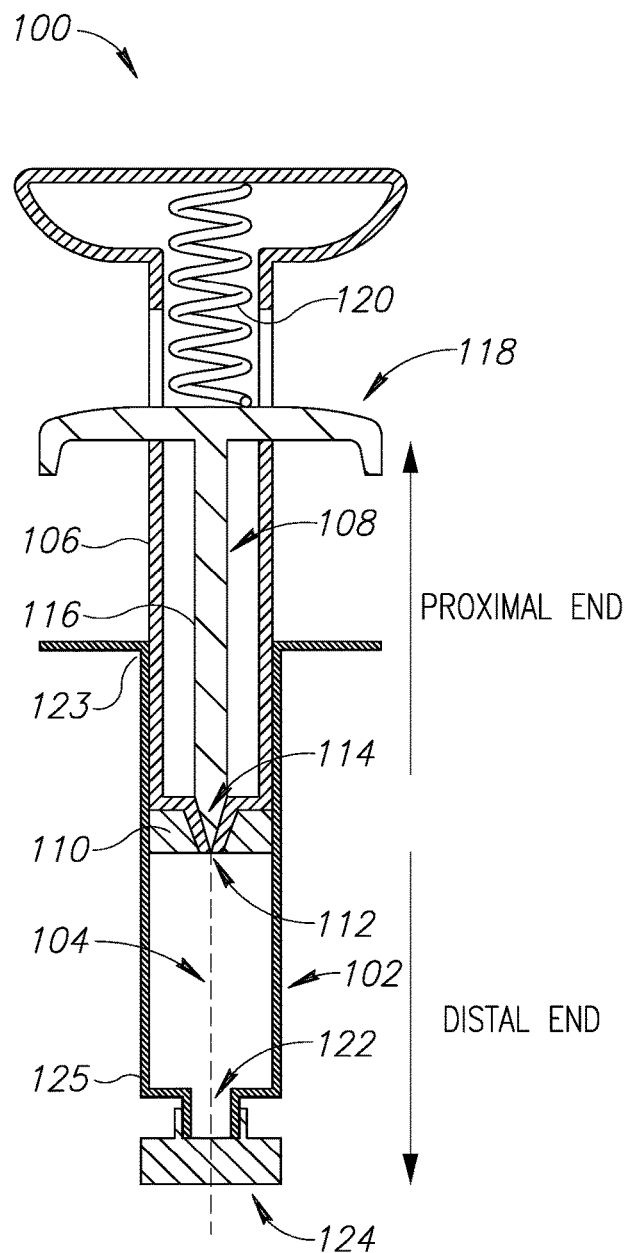
FIGS. 1a and 1b illustrate schematic drawings of the dual chamber syringe in closed and open position respectively.

FIG. 1a illustrates a dual chamber syringe 100 according to the present invention. A first main chamber 104 is defined by the interior portion of syringe barrel 102. As can be appreciated by reviewing FIG. 1a, the syringe barrel 102 has a fixed maximum volume. However, the effective volume, that is, the volume which is available to contain material, is defined by the position of the syringe piston 106 positioned within the barrel 102. The syringe piston 106, in a conventional manner, can slidably and sealably move within the syringe barrel 102. The syringe piston 106 position within the barrel may change the effective volume of the main chamber 104 to anywhere from its maximum volume to zero should the piston be pushed towards the distal end 125 of the barrel. According to the present invention, the syringe piston 106 is of a hallow construction. The hollow piston 106 defines therein a sealed and slidable moving secondary chamber 108. The slidable secondary chamber 108 changes the effective volume of the main chamber 104 due to the movement of the piston from the proximal end 123 of the barrel to its distal end 125. The main chamber 104 of the syringe and the secondary chamber 108 of the syringe are separated by a barrier 110. The barrier has an aperture 112 which may establish a fluid communication between the main chamber 104 and secondary 108 chambers. The aperture 112 may be sealed by a movable sealing element 114.

Figure 1B:
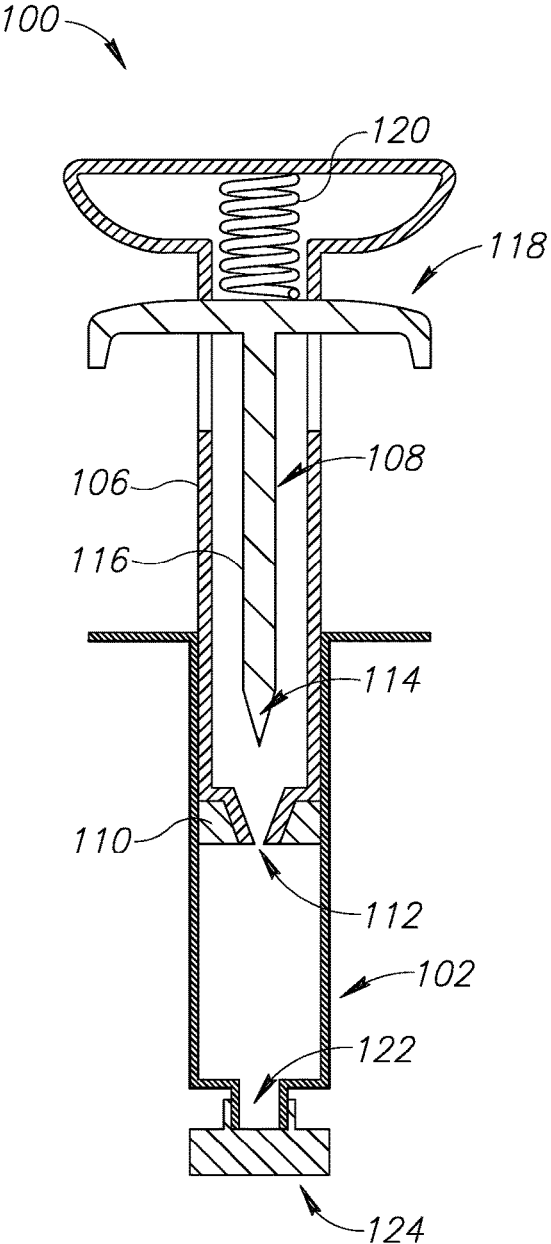

The movable sealing element 114 is configured to seal the aperture 112, through the operation of a mechanism which may be contained within the secondary chamber 108. The sealing element 114 may be connected to a shaft 116 extending along the axis of the secondary chamber and out of the proximal end 123 of the secondary chamber 108. The shaft 116 is configured to move the sealing element 114 from a sealed-closed position as shown in FIG. 1a to an open position by pulling a shaft grip 118 to compress a spring 120 as shown in FIG. 1b In the illustrated embodiment of FIGS. 1a and 1b, the spring 120 may be seen to be of a type that pushes the shaft 116 in a distal direction 125 to keep the sealing element 114 in contact with the barrier 110. In the closed position as shown in FIG. 1a there is no fluid communication between the main chamber 104 and secondary chamber 108 of the syringe 100. In the open position as shown in FIG. 1b, in which the shaft 116 has been pulled by the grip 118 in a proximal direction 123 against the bias of the spring 120, fluid communication is established between the main chamber 104 and the secondary chamber 108. With this configuration, unlike those of prior art syringes, multiple, controllable movements of material between the main chamber 104 and the secondary chamber 108.

The mechanism of action of the syringe 100 and a method for PRP preparation in accordance to one aspect of the present invention will now be described. A barrel discharge opening 122, which is configured to connect to a standard needle, is positioned on the distal end 125 of the barrel and may be sealed by a cap 124. By uncapping the discharge opening 122 can be connected to any needle for the purpose of withdrawing the blood. While the shaft 116 is sealing the aperture 112 the blood will be contained in the main chamber 104. The blood can be separated to layers of red blood cells, white blood cells and platelets, and plasma by centrifuging the capped syringe 100 with the blood content through any conventional centrifuge. After the centrifugation the layers will be separated according to the specific gravity of each component. For separating the red blood cells from the white blood cells, platelets and plasma the following procedure may be performed with the syringe: while keeping the discharge opening 122 sealed with the cap 124, the shaft 116 is manually manipulated in a proximal direction 123 to move the sealing element 114 out of the aperture 112. While maintaining aperture 112 open, the piston 106 is pushed in a distal direction 125 against the layers in the main chamber 104 in order to decrease the free volume of the main chamber 104. The layers located in the proximal end 123 of the main chamber 104 will be moved to the secondary chamber 108. When reaching the limit line between the red blood layer and the white cells-plasma layer the shaft grip 118 is released to allow the sealing of the aperture 112 by the sealing element 114. The cap 124 is removed from the syringe 100 and the piston 106 is pushed towards the distal direction 125 to extrude the red blood cells layer. The syringe 100 is capped again with the cap 124 and the shaft 116 is manipulated again towards the proximal end 123 to unseal the aperture 112 and establish the fluid communication again between the main 104 and the secondary 108 chambers. By keeping the aperture 112 open and by retracting the hollowed piston 106 back, since the barrel head 122 is sealed, vacuum is established in the newly-formed free space in the main chamber 104 which in turn sucks the white cells, platelets and plasma layer to into the main chamber 104. The centrifugation process can be done again to the content of the main chamber 104, this will allow a further concentration of the platelets as its specific gravity is higher than the plasma. The same process of separation between layers into two chambers can be done again to separate the platelets layer in the main chamber 104 from the plasma layer in the secondary chamber 108. The PRP layer is now ready to be applied to any area by connecting the barrel head 122 to any of the delivery systems further described in FIG. 2 to FIG. 9.

Topical Application Delivery Systems

Figure 2:
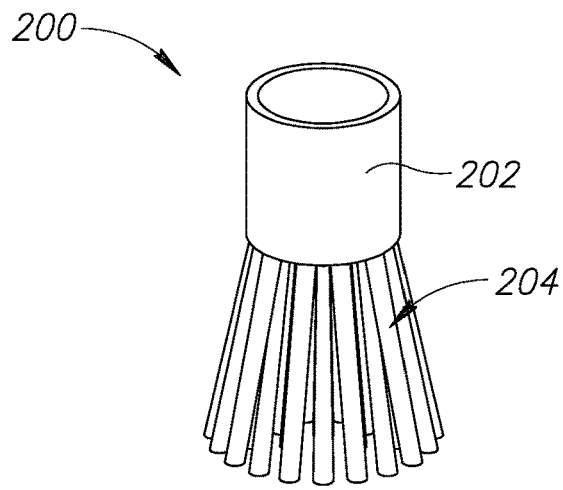
FIG. 2 illustrates a schematic drawing of a brush delivery system to be connected to the dual chamber syringe.

FIG. 2 illustrates a brush delivery system 200 that can be connected through a luer lock opening 202 to any matching connection. The material can be pushed through the luer lock opening 202 towards the bristles 204. By moving the bristles 204 on any surface, the material will be spread to form a layer topically covering the surface.

Figure 3:
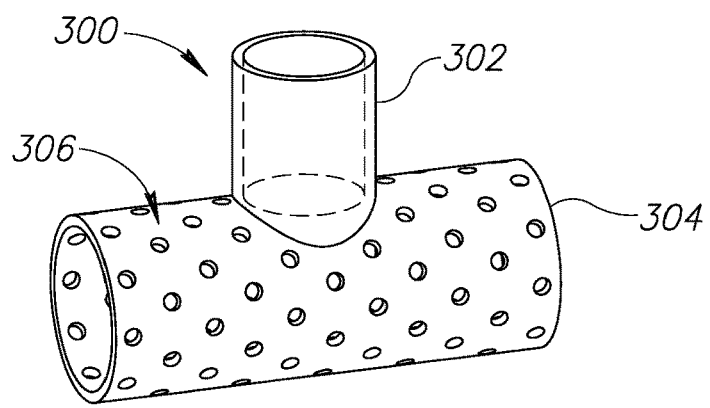
FIG. 3 illustrates a schematic drawing of a sponge delivery system to be connected to the dual chamber syringe.

FIG. 3 illustrates an embodiment of sponge delivery system 300. The sponge delivery system 300 can be connected through a luer lock opening 302 to any matching connection. The material passes through the luer lock opening 302 towards a sponge head 304, the sponge head consists of pores 306 having either the same size or different sizes. The pores 306 will deliver the material contained in them when pushed against any surface as the sponge head 304 will compress and squeeze the material inside the pores 306.

Figure 4:
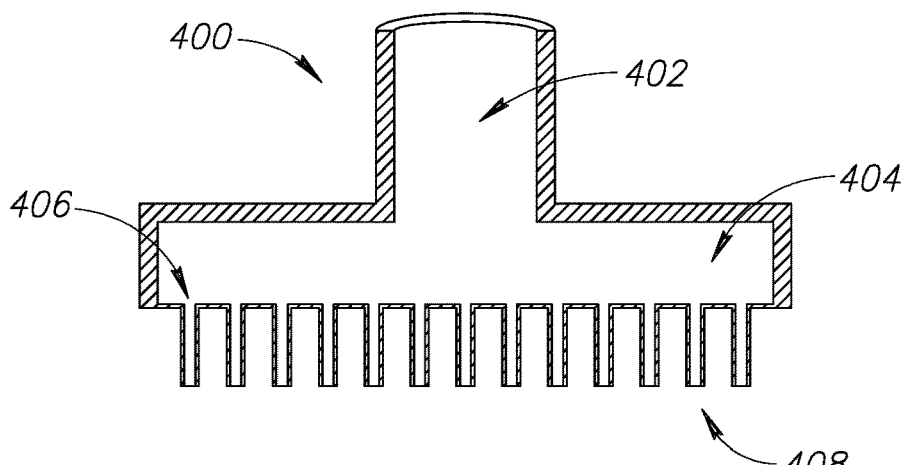
FIG. 4 illustrates a schematic drawing of a flexible brush delivery system to be connected to the dual chamber syringe.

FIG. 4 illustrates a flexible brush delivery system 400. The flexible brush delivery system 400 can be connected through a luer lock opening 402 to any matching connection. The material passes through the luer lock opening 402 to a container 404. The material will be delivered through flexible filaments 408 by passing through flexible filaments openings 406. Each of the flexible filaments 408 will apply the same amount of material on any surface by moving the flexible filaments 408 in the desired direction in parallel to the surface.

Figure 5A:
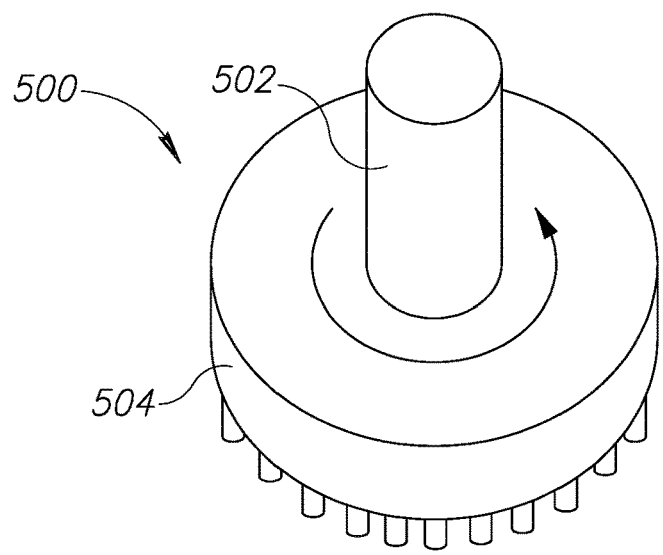
FIGS. 5a and 5b illustrate schematic drawings of a spiral delivery system to be connected to the dual chamber syringe.
Figure 5B:
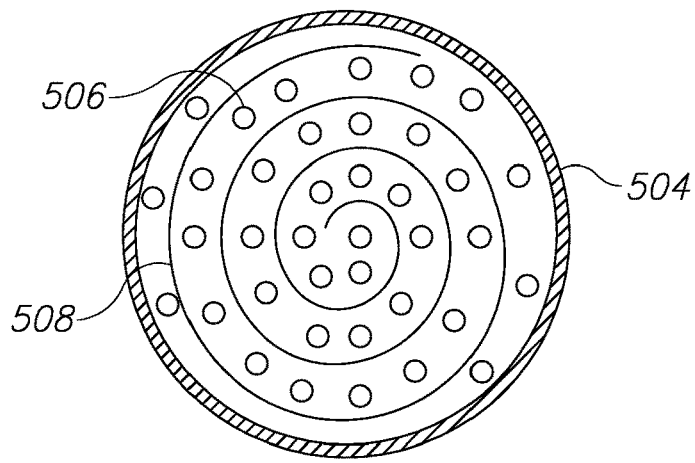

FIG. 5a illustrates a spiral delivery system 500. The spiral delivery system 500 can be connected through a luer lock opening 502 to any matching connection. The material passes through the luer lock opening 502 towards a head 504. FIG. 5b shows a bottom view of the head 504, the material extrudes through the apertures 506 while a spiral protrusion 508 spread the material on the surface. The head 504 can be moved in any direction in parallel to the surface and can also be rotated for applying circular massage on the surface.

Figure 6:
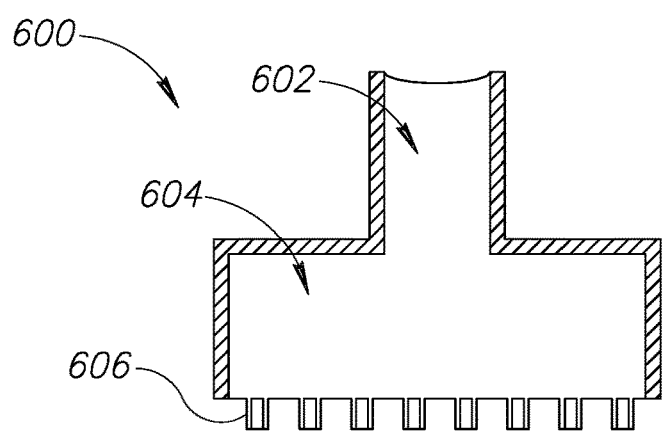
FIG. 6 illustrates a schematic drawing of a ballpoint head delivery system to be connected to the dual chamber syringe.

FIG. 6 illustrates an embodiment for a ballpoint head delivery system 600. The ballpoint head delivery system can be connected through a luer lock opening 602 to any matching connection. The material passes through a container 604 and divides to balls openings 606 for being extruded and applied to the surface. The balls openings 606 may be made of rigid material for applying a massage to the surface being pushed against. A vibrational movement can be combined with the parallel movement of the ballpoint head delivery system 600 for applying a massage and assist in improving the diffusion of the material through the surface.

Injection Delivery Systems

The following embodiments describe delivery systems for injection to different skin layers as the needle's length in any of the embodiments can be changed to allow the penetration to desired skin layer and the application of any material especially PRP. Needles described herein may also be configured to deliver radio frequency (RF) treatment to the skin into any of the skin layers as known to the skilled person in the art. A combined PRP and RF treatment may be done by injecting PRP to the site of RF treatment before, during or after the injection of the PRP. RF needles may have one or more conductive surfaces (electrodes) configured to deliver RF energy to the skin. One such conductive electrode may be located at the tip of the needle proximal to its injecting end. In this case the PRP and RF targets adjacent tissue on approximately the same skin layer. According to another aspect of the invention, conductive electrodes may be located proximally to the tip of the needle configured to deliver RF energy to tissue area located above the tissue which is targeted by the PRP. In a combined RF and PRP treatment, PRP should be protected thermally to avoid thermal damage to the PRP. According to one aspect of the invention, needle array may be divided into at least two groups. At least one group of needles may be configured to deliver RF treatment only while at least one group of needles may be configured to deliver PRP only. As mentioned above, another way to protect the PRP from the elevated temperature of the RF treatment may be achieved by keeping a certain distance along the needle between the PRP needle delivery end and the location of the RF electrode of such micro-needle. During operation, PRP injection and RF treatment may be delivered into the tissue in a sequence which is designed to avoid overheating of the PRP, whether located in a delivery system or already injected into the tissue, either by cooling the delivery system and/or the tissue or by allowing the heat to diffuse from the needle or tissue before PRP is delivered through or into it. According to another aspect of the invention a combined fractional RF treatment may be delivered before during or after the delivery of the PRP.

Figure 7:
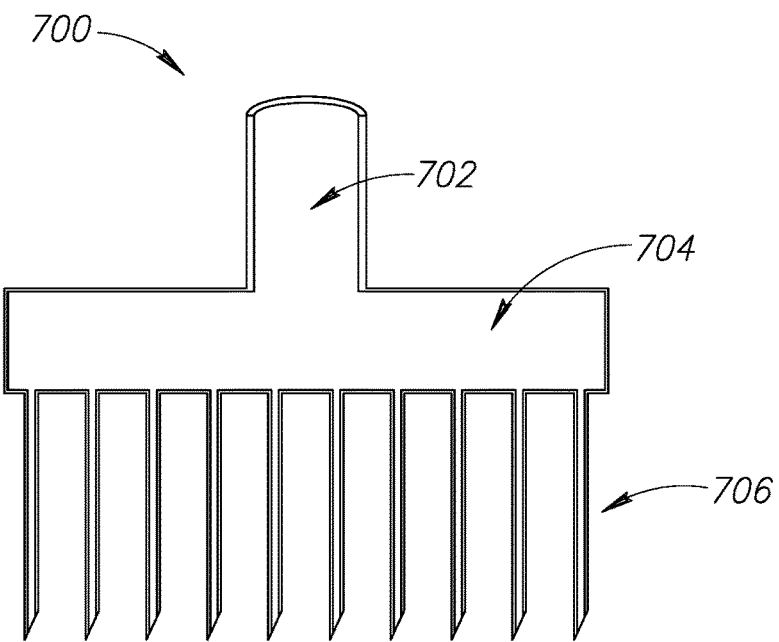
FIG. 7 illustrates a schematic drawing of a micro-needles delivery system to be connected to the dual chamber syringe.

FIG. 7 illustrates an embodiment for micro-needles delivery system 700. The micro-needles delivery system 700 can be connected through a luer lock opening 702 to matching connection. The material can be pushed through the luer lock opening 702 towards the container 704. The material will be divided and extruded micro-needles 706 as the same portion will be delivered by each needle to the skin layer where the micro-needles 706 tip is positioned.

Figure 8A:
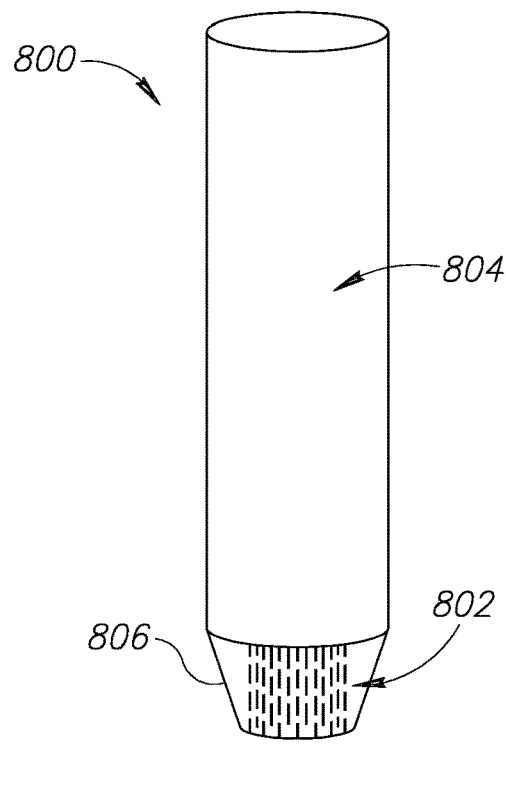
FIGS. 8a and 8b illustrate a schematic drawing of a micro-needles pen delivery system to be connected to the dual chamber syringe.
Figure 8B:
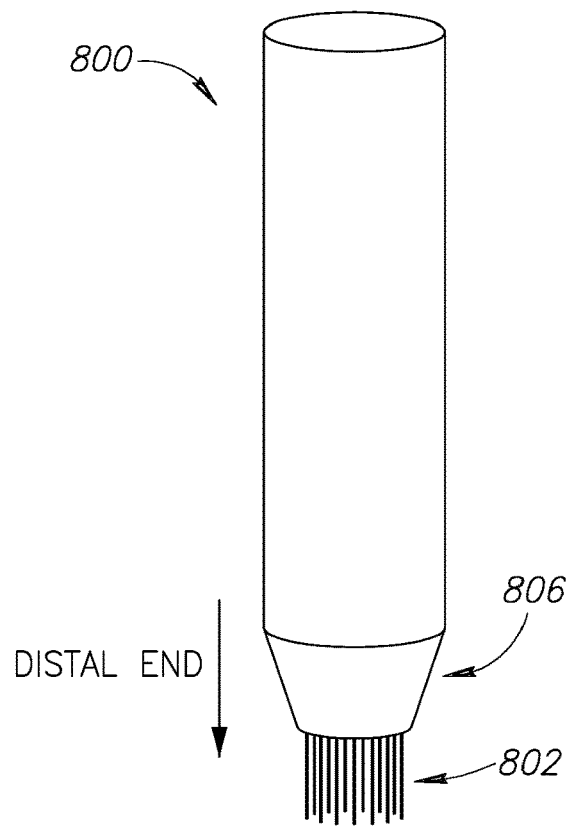

FIG. 8a described a micro-needles pen delivery system 800. the micro-needles pen delivery system 800 extrudes the material through micro-needles 802. Any syringe can be inserted to a container 804 where the material can be pushed manually or automatically from the syringe towards the micro-needles 802. In a closed position, the micro-needles 802 are covered with a safety ring 806 to secure the micro-needles 802 and prevent the penetration to an undesired surface. In an open position, as shown in FIG. 8b, the micro-needles 802 will be pushed towards the distal end of the micro-needles pen delivery system 800 and can be penetrated to the skin. The micro-needles pen delivery system 800 can either be manually operated to allow the penetration of the micro-needles 802 through the skin, or automatically operated by controlling the speed of the penetration and un-penetration of the micro-needles 802 through the skin layers. The automatic operation of the needles pen delivery system 800 is thought to maximize the efficiency of the treatment and reduce the pain of the micro-needles 802 penetration.

Figure 9A:
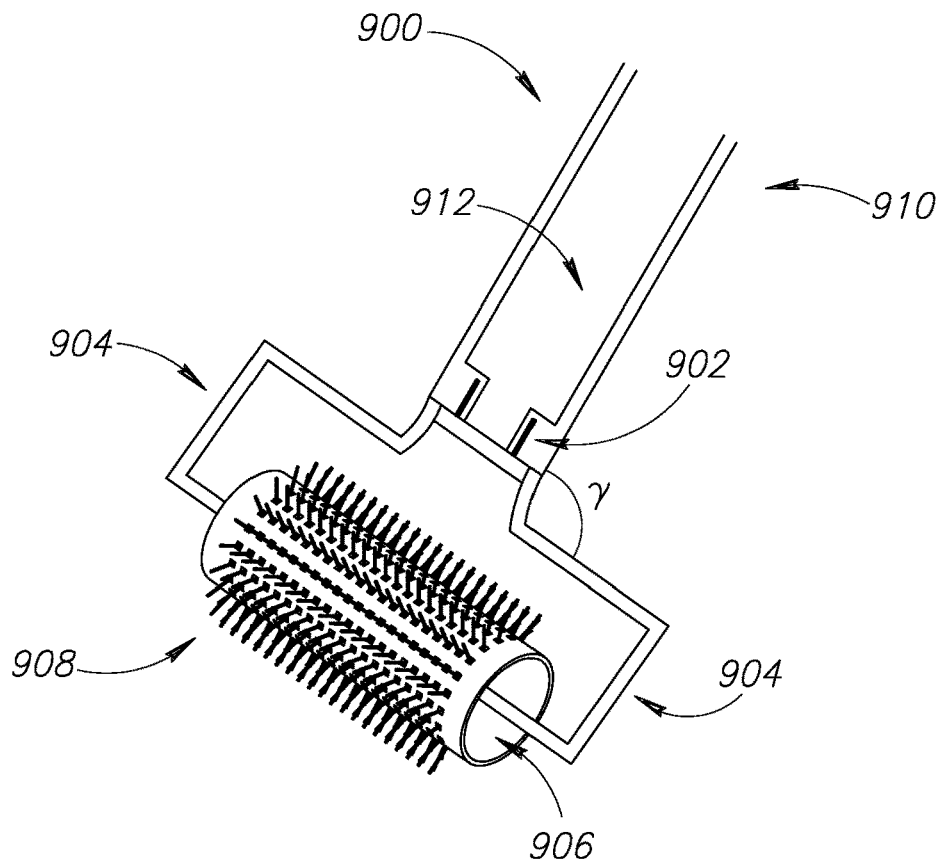
FIGS. 9a and 9b illustrate schematic drawings of a micro-needles roller delivery system to be connected to the dual chamber syringe.
Figure 9B:
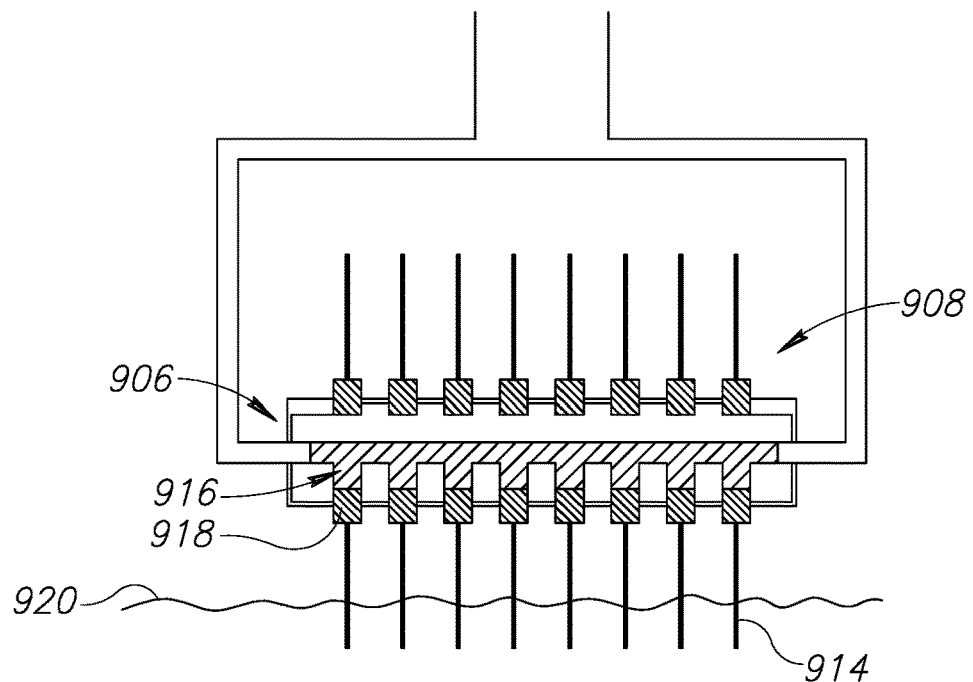

FIG. 9a illustrates a micro-needle roller delivery system 900. The micro-needle roller delivery system 900 can be connected to any syringe by a luer lock opening 902. The material is pushed and extruded through a hollowed channel 904 to reach a roller head 906. The roller head 906 consists of micro-needles 908 that covers the outer surface area. the micro-needles 908 deliver the material only through the needles row that penetrates the surface, the mechanism of action for this device will be further described below: the user grabs a handle 910 that is connected to the hollowed channel 904 and the roller head 906 by a fixed angle γ that allows convenient grip for moving the roller head 906 against a parallel surface. By manually or automatically controlling the material passage from a container 912, the material will pass through the luer lock opening 902 and the hollowed channel 904, reaching the roller head 906 and will be injected through the micro-needles 908 only to the penetrated surface area. by moving the handle 910 in parallel to the surface, the roller head 906 will rotate and allows the penetration of new row of micro-needles 908 to the surface when the last row will now deliver the material while all the others row are sealed. FIG. 9*b* shows a detailed illustration for the mechanism of passing the material only through the penetrating micro-needles row 914. The roller head 906 consists of openings 916 directed and fixed perpendicular to the surface 920. When the micro-needles 908 rotates, micro-needle row openings 918 become conjugated with the openings 916 and allow the passage of the material through this micro-needles row 914. in the phase of rotating the roller head 906 to move between different micro-needles rows 908, the openings 916 is sealed by the roller head 906 inner wall and do not allow the passage of the material.

Figure 10A:
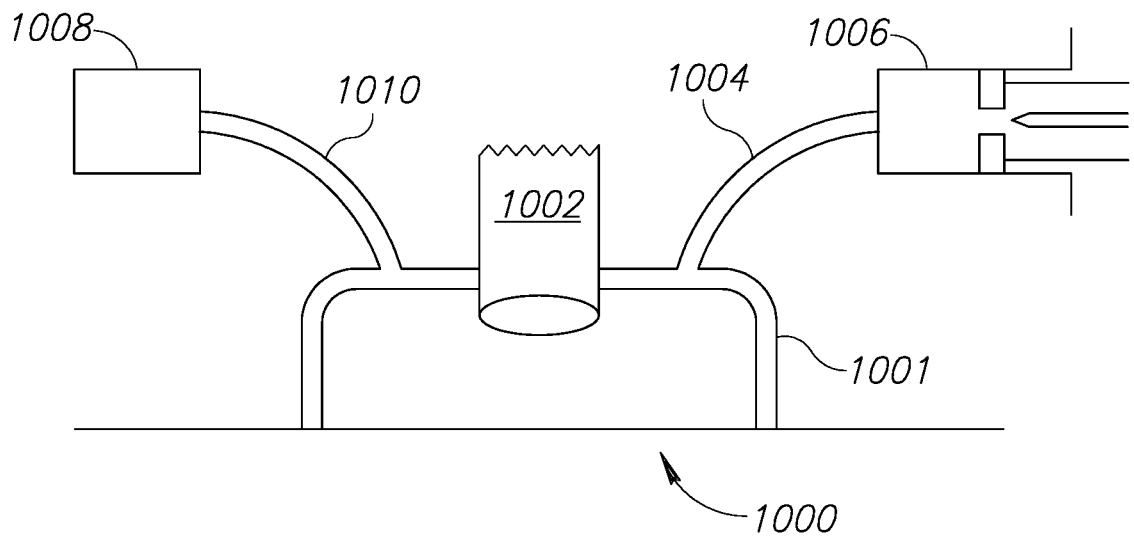
FIGS. 10A and 10B illustrate an embodiment for combining PRP delivery in connection with a fractional laser treatment.
Figure 10B:
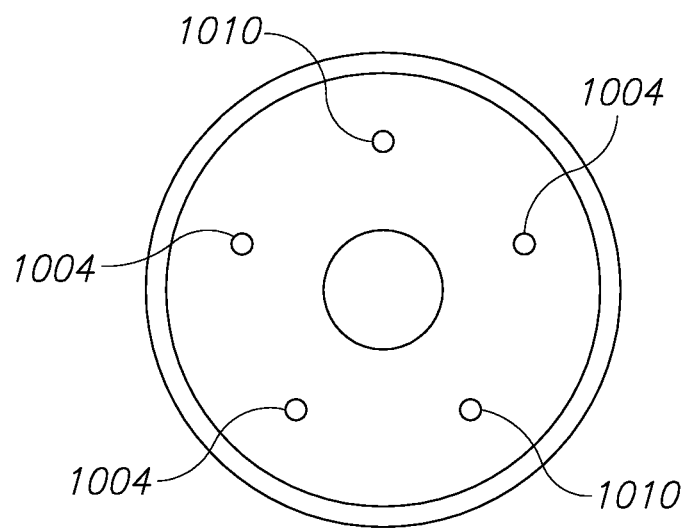

FIGS. 10A and 10B illustrate the application of PRP or other material in combination with a laser fractional treatment. As can be seen in the figures, a housing 1001 may be placed in contact with the skin surface 1000. The housing 1001 may include a laser fractional treatment head 1002 which may be of any known type, including the fractional treatment apparatus described in US 2012/0065551, the entirety of which is herein incorporated by reference. The housing 1001 along may include a syringe 1006 of the type described in the present application connected by tubing 1004 to an outlet within housing 1001. In addition, a source of pressure and/or vacuum 1008 with its conduit 1010 may also be connected to the housing 1001, as seen by the openings 1004, 1010 in FIG. 10B.

In operation, the fractional laser 1002 may be activated and either before, simultaneously with or after the fractional laser has been activated, the syringe, which may contain a supply of PRP, also activated by pushing on a plunger manually or using suitable mechanical devices. Thus, as "channels" are formed in the skin surface 1000 by the fractional laser, amounts of, for example, PRP may be forced into those formed "channels" before the channels close following laser activation. The source of pressure/vacuum may also be activated to enhance delivery of the PRP into the "channels" formed.

Figure 11:
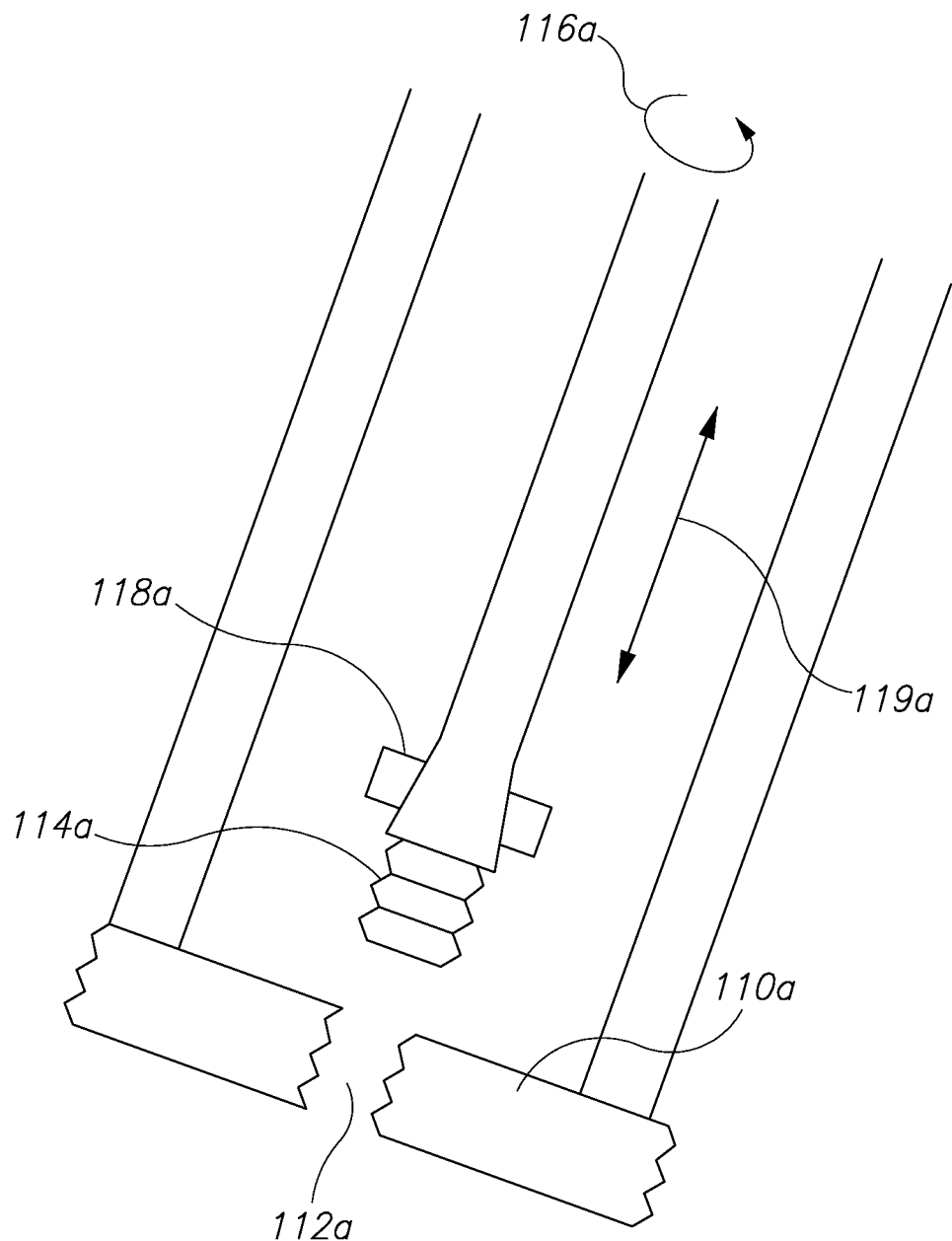
FIG. 11 illustrates an alternative embodiment of a sealing element for the syringe of FIGS. 1a and b.

FIG. 11 illustrates an alternative arrangement of the movable sealing element 114 of FIGS. 1*a* and 1*b*. In FIG. 11, in place of the conically-shaped sealing element 114 which mates with a similarly shaped aperture in barrier 110, an externally-threaded sealing element 114*a* mates with an internally-threaded opening 112*a* in barrier 110*a*. A further sealing flange 118*a* is placed proximally of the sealing element 114*a* to assure good sealing quality. In operation, in order to allow contents of the main syringe body to enter or be mixed with contents in the syringe piston (as those elements are shown in FIGS. 1*a* and 1*b*), the threaded element 114*a* is turned, by way of example, in the direction 116*a*. This causes the threaded element to disengage from the barrier 100, and then be able to be moved in the directions 119*a*. This arrangement may be particularly useful for applications in which separation of the two chambers must be assured, such as in the delivery of drugs whose powder and liquid components must be kept separated until mixed and administered.

Further Syringe Embodiments

Turning now to FIGS. 12A and 12B, these figures illustrate a second syringe embodiment 1200. Like the syringe 100 of FIGS. 1*a* and 1*b*, the syringe 1200 includes a syringe barrel 1202 and a needle 1204. The syringe also includes a syringe piston 1210 which is fitted within barrel 1202. Like the syringe barrel 106 of FIG. 1*a*, the syringe barrel 1202 is not solid but hollow and capable of containing materials. At the distal end 1205 of the barrel is fixed by any suitable means (like gluing, heat shrinking, etc.) a stopper 1214 with one or more apertures or a holes therethrough formed along an axis parallel to the barrel longitudinal axis. The stopper 1214, like its counterpart 112 of FIG. 1*a*, is made to fit at the distal end of the barrel and prevent the escape of fluids either to outside of the syringe or into the piston 1210 internal volume.

The piston 1210 shown in FIG. 12A includes an external screw thread 1209 formed on the outside of the barrel and covering the majority of the barrel. In an alternative arrangement, instead of an external screw thread an internal screw thread 1211 may be formed into the barrel 1212 of FIG. 12A. In addition, an engageable switch 1208 seen in FIGS. 12A and 12B includes a holder 1206 which mounts the engageable switch on the syringe barrel 1202. The holder and engageable switch may be mounted on syringe barrel by any suitable joining device, such glue or heatshrinking or welding. When mounted in the holder 1206, the switch 1208 is movable in directions 1219. The switch 1208 may also include an engaging tooth 1218. While one tooth is shown in FIG. 12B, it is to be understood that a greater number may be employed.

The purpose of the engaging tooth 1218 is to selectively engage either the internal screw threads 1211 or the external screw threads 1209. The interaction of the tooth 1218 and the internal or external threads 1209 or 1211 will be explained below. FIG. 12A also illustrates a shaft 1216 that fits within the internal space of the barrel 1210 or 1212 and is insertable though the proximal end 1207 of barrel 1210. As mentioned, the stopper 1214 includes a hole 1215 therethrough (see FIG. 12C) along the central axis of the barrel 1210 that allows or restricts the passage of fluids from the syringe barrel interior to the interior of the barrel 1210 and vice versa. Whether fluids may flow or not flow between the barrels is determined by the position of shaft 1216. Shaft 1216 at its distal end includes a protruding member 1220. The shaft 1216 is movable in directions 1222 within the barrel 1210. Movement may be by way of a screw thread 1224 which interacts with a complementary screw thread (not shown) within the barrel 1210 and may be located towards the proximal end 1207 of the barrel. Other devices, such as a pressure fitted shaft may be implemented. In any case, turning the shaft in a clockwise direction 1225 may cause the shaft to move in direction 1226 within the barrel 1210. At some point the protruding member 1220 will enter the hole or aperture in the stopper or the hole in the distal end 1205 of the barrel and prevent fluid interaction between the two chambers. Turning the shaft in the opposite direction will permit fluid communication between the two chambers. A left hand or a right hand screw may be implemented as desired.

Unlike the embodiment of FIGS. 1*a* and 1*b*, the embodiment of FIGS. 12A and 12B has the advantage of less parts and less moving parts. In the embodiment of FIGS. 1*a* and 1*b*, as described above, after each centrifugation, the process of separation of components is done by pushing the inner barrel in a distal direction towards the distal end (see FIG. 1*a*). It may be difficult to precisely gauge where one type of blood component ends and a second type begins. This is true for the first centrifugation to discern the red blood cells/white cells-plasma line and in the second centrifugation to discern the line between platelet rich and platelet poor plasma. With the simple "push-pull" of the inner barrel in the FIG. 1a embodiment, it may be easy to "overshoot" the line and that may cause undesirable mixing of blood components.

In the embodiments of FIGS. 12A and 12B, the syringe may be used in either a "push-pull" mode or a more precise "screw" mode. For example, after centrifuging the second time, the inner barrel may be advanced in a distal direction 1228 by pushing. However, as the distal portion of the inner barrel approaches the rich/poor PRP line, the user may move engageable switch 1208 to cause tooth 1218 to enter into or between internal or external threads 1209 or 1211. Once this is done, the barrel can no longer be pushed in a distal direction or the opposite direction in fact. However, by turning the inner barrel by grasping knurled knob 1230 and turning it in a clockwise direction (if a right—hand groove or screw thread), will cause the inner barrel to advance in a distal direction in a more controlled manner so as to prevent the type of intermixing discussed above. When the "screw" function is not needed, such as, for example, when blood is being taken from the patient, the tooth is disengaged from the threads 1209 or 1211. The embodiment of FIGS. 12A and 12B also does away with the spring 120 shown in FIG. 1a and the need to compress and hold the spring 120 in a compressed state in certain operations, thus allowing the blood separation process to be smoother with the simple "on/off" screw arrangement in the shaft 1216 described above.

Once the needle 1204 has been removed from the distal end of barrel 1202, any of the application accessories shown in FIGS. 2 through 9b may be fitted onto the distal end which can then dispense PRP onto a skin or other tissue site. A luer-type lock may be fitted or otherwise incorporated onto the distal end to accommodate these accessories. Also, once needle 1204 has been removed the syringe may be fitted onto connector 1004 of the fractional energy deliver device shown in FIGS. 10A and 10B.

The mechanism of action of the syringe 1200 and a method for PRP preparation in accordance to one aspect of the present invention will now be described. A barrel discharge opening is configured to connect to a standard needle 1204, and is positioned on the distal end of the barrel 1202 and may be sealed by a cap, not shown but similar to cap 124 in FIG. 1a. By removing the cap, the discharge opening of the distal end of barrel 1202 can be connected to any needle for the purpose of withdrawing blood while the shaft 1216 and its protuberance 1220 is sealing the aperture in the stopper 1214 so that blood will be contained in the main chamber of barrel 1202. The blood can be separated into layers of red blood cells, white blood cells, platelets and plasma by centrifuging the capped syringe 1200 with the blood content through any conventional centrifuge.

After a first centrifugation, the layers will be separated according to the specific gravity of each component. For separating the red blood cells from the white blood cells, platelets and plasma the following procedure may be performed with the syringe: while keeping the barrel head sealed with the cap, the shaft 1216 is manually manipulated in a proximal direction by turning it in a direction opposite to arrow 1225 (for a right hand thread) to move the sealing element 1220 out of the aperture in the stopper 1214 or the aperture in distal end 1205. While maintaining the aperture open, the piston 1210/1211 is pushed in a distal direction 1226 against the layers in the main chamber in order to decrease the free volume of the main chamber of outer barrel 1202. This may be done by either pushing the barrel 1210/1211 in a distal direction and/or engaging the threads 1209/1211 on the barrels 1210/1211 respectively with the tooth 1218 of assembly 1208 by moving it in a direction so that the tooth enters the threads 1209/1211. Using the threads allows for very precise movements so that only those blood components (like PRP) enter into the barrel 1210/1212. The layers located in the proximal portion of the outer barrel will thus be moved to the secondary chamber 1210/1212.

When reaching the limit line between the red blood layer and the white cells-plasma layer, the shaft 1216 is turned in direction 1225 to seal the aperture in the stopper 1214 by the sealing protuberance 1220. The cap is then removed from the syringe 1200 and the piston 1210/1211 is pushed towards the distal direction 1226 to extrude the red blood cells layer from the barrel 1202. The syringe is then capped again with the cap and the shaft 1216 is moved again in a proximal opposite direction 1226 to unseal the aperture in the stopper 1214 and establish fluid communication again between the main barrel 1202 and the secondary barrel 1210/1211.

By keeping the aperture in the stopper 1214 open and by retracting the secondary piston 1210/1212 back, since the distal end of the barrel 1202 is sealed, vacuum is established in the newly-formed free space in the main chamber of barrel 1202 which in turn sucks the white cells, platelets and plasma layer to into the main chamber of the barrel 1202. The centrifugation process can be repeated again to the contents of the main chamber of the barrel 1202. This will allow a further concentration of the platelets because its specific gravity is higher than that of the plasma. The same process of separation between layers into two chambers can be done again to separate the platelets layer in the main chamber of the barrel 1202 from the plasma layer in the secondary chamber of barrel 1210/1212. The PRP layer is now ready to be applied to an of skin or tissue area by connecting the distal end of barrel 1202 to any of the delivery systems described in FIG. 2 to FIGS. 10a/b.

After the second centrifugation, the blood components left behind include a volume of Platelet Rich Plasma (PRP) as well as Platelet Poor Plasma (PPP). Rather than dispose of the PPP, the PPP may be extracted from the syringe and used in known processes to produce fibrin that may be used to seal wounds or the like into which, for example, PRP has been applied, or, in an alternate manner, the PPP is first applied followed by the PRP onto or into the designed skin or other tissue.

In addition, in the event that a dual barrel structure is not required, but only a single (outer) barrel, the mechanism shown in FIG. 12A with the internal or external threads illustrated on a syringe piston may be retained as well as the locking mechanism described above. In this manner, in those instances of injection/application of fluids is desired to be better controlled or metered than with a simple push movement, which has potential problems of injecting a patient with greater a quantity of medicine or other fluid than desired, the screw threads may be engaged and the medicine or fluid dispensed in a controlled manner by rotating the threaded syringe piston. Thus, in the above embodiment, the inner mechanisms within the syringe piston are dispensed with.

Administration of PPP and PRP During Fractional Treatment of the Skin

Figure 13:
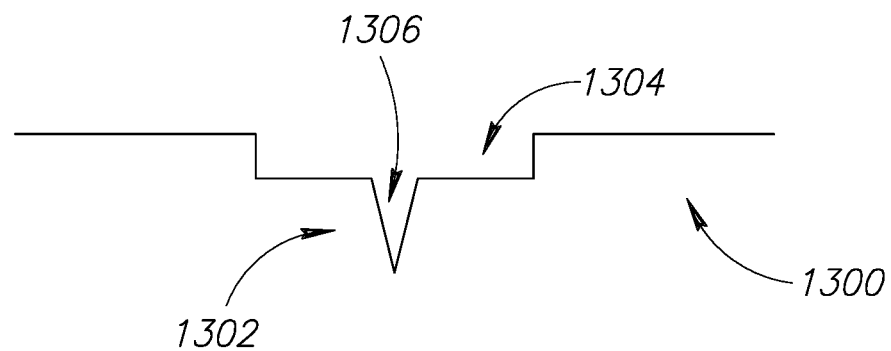
FIG. 13 illustrates a section of the skin after fractional laser treatment.

FIGS. 10A and 10B illustrate and the accompanying text describes combining PRP with fractional treatment. FIG. 14, discussed below, further describes this type of treatment but also adds treatment using PPP. FIG. 13 illustrates a section of skin after laser fractional treatment 1300. Fraction laser treatment may be manipulated to create different channel shapes in the skin. One channel shape 1302 as shown here contains two distinct hole shapes; a shallow big hole 1304 and a deep narrow hole 1306. While the deep hole 1306 is shown as being V-shaped, it is to be understood that any suitable shape may be created and formed in the skin. PRP and PPP may be applied to the channel 1302 using various methods to induce skin rejuvenation and wound healing. A first method includes applying PPP after its activation, with Thrombin or similar compounds that converts fibrinogen to fibrin, in the shallow broader hole 1304. Activated PPP creates a sealant layer on the skin and enters the channel 1302. The sealant prevents the channels from collapsing after treatment. Other methods may combine the application of PPP with PRP. Following the application of PPP, the PRP is applied above the sealant layer and diffuses through the channel 1302 to reach the deep narrow hole 1306.

In the same manner, the PRP may be applied to the skin 1300 prior to the PPP application. The PRP diffuses through to the deep narrow hole 1306 and initiates the rejuvenation process. Then, the PPP is activated and applied to the skin 1300. The PPP enters the channel 1302 and seals the shallow broader hole 1304.

Finally, the PRP and PPP may be mixed before the application and applied simultaneously to the skin 1300.

Figure 14A:
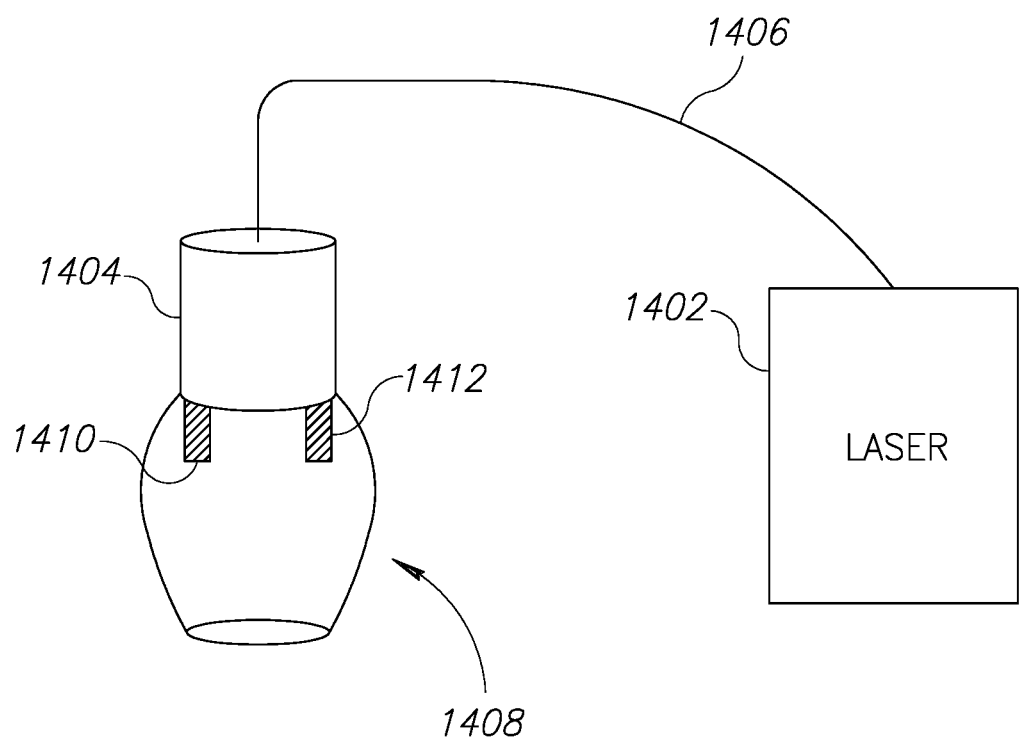
FIGS. 14A and 14B illustrate a laser treatment system and handle combined with PRP and PPP treatment.

FIG. 14A illustrates laser treatment system combined with PRP and PPP application. The laser system 1402 is connected to a handle 1404 through a delivery mean 1406. The delivery mean 1406 delivers the laser energy to the handle 1404. The handle 1404 is connected to a disposable housing 1408 that contacts the patient skin during the treatment. The disposable housing covers two nozzles 1410 and 1412 that apply PPP and PRP to the skin during the treatment.

Figure 14B:
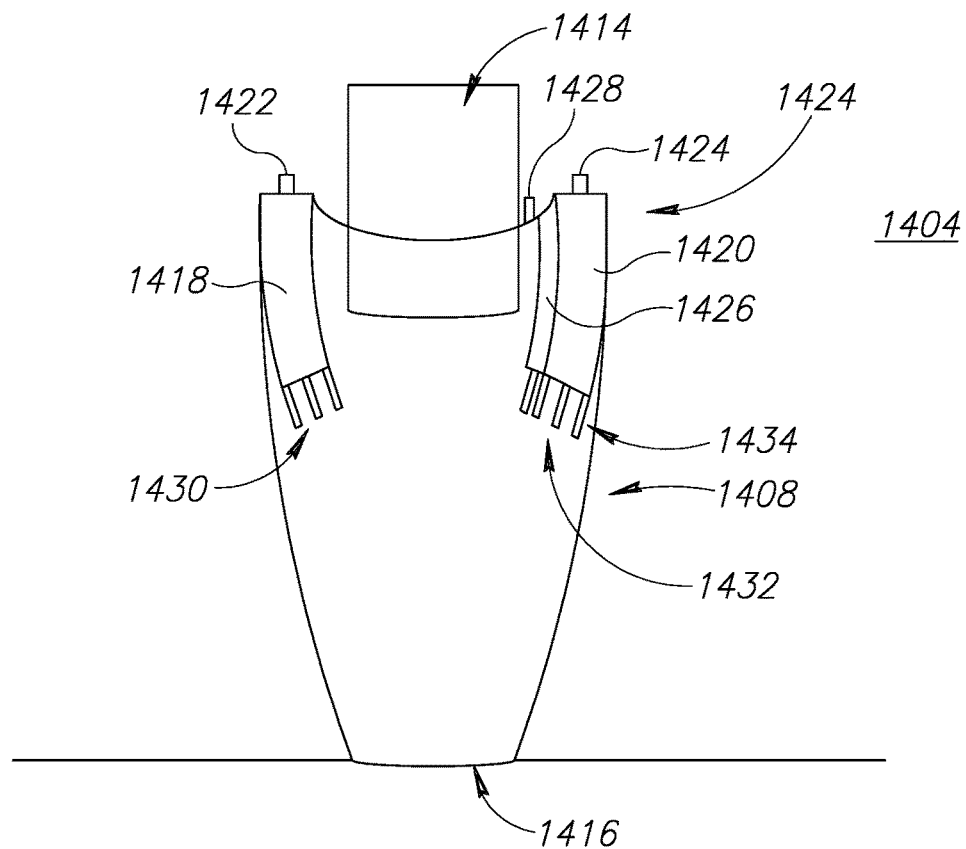

FIG. 14B illustrates one embodiment of the handle 1404 for applying PPP and PRP using air pressure. The handle 1404 includes the disposable housing 1408 that is connected to a laser scanner or beam splitter 1414. The laser scanner 1414 receives the laser energy and apply it fractionally to a section of skin 1416. The disposable housing covers at least one PRP nozzle 1418, at least one PPP nozzle 1420 and at least one activator nozzle 1426. PPP nozzle 1420 and PRP nozzle 1418 apply the PPP and PRP respectively during or after the treatment to the skin section 1416. The PRP and PPP are inserted into the nozzles 1418 and 1420 through sealed rubber barriers 1422 and 1424 respectively to prevent contamination of the materials. To activate the PPP, an activator such as thrombin is inserted through nozzle 1426 and is separated from the PPP nozzle 1420. The activation of PPP will be initiated after the application of the PPP and the activator. For delivering PPP, PRP and activator, air pressure is applied inside the disposable housing 1408 through an air pressure aperture 1428. The air pressure allows spraying of PRP, PPP and activator from at least one aperture for each material 1430, 1432 and 1434. When spraying, the materials are mixed and the PPP is activated.

Treatment of Cellulite

Figure 15A:
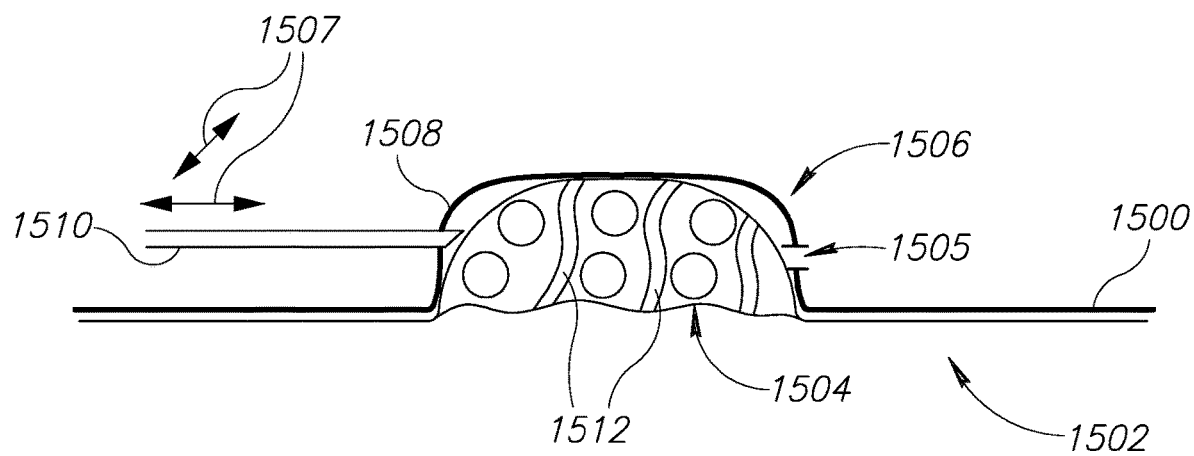
FIGS. 15A, 15B, 15C, 15D illustrate a method of treating cellulite combined with PRP and PPP treatment.

Cellulite is the accumulation of fat within a connective tissue. The fat grows and causes alterations of the topography of the skin that are characterized by a padded "bumps" appearance. Many treatments aim to disconnect the connective tissue to allow a smoother appearance of the skin. These treatments are mostly invasive and require a long recovery time. FIG. 15A illustrates a method of treating cellulite combined with PRP and PPP application. The treatment device 1500 is placed on a section of skin 1502. Part of the skin 1504 is sucked into chamber 1506 in the treatment device 1500. The chamber 1506 includes a port 1505 which is attached to a source of vacuum to draw the skin 1504 into the chamber 1506 of treatment. The chamber includes a sealable aperture 1508 to allow the insertion of a needle 1510 and for it to move it back and forth and/or horizontally to the sides within the chamber 1506. The needle 1510 is inserted into the aperture 1508 and invasively enters the part of skin 1504. The needle moves in x-y direction 1507. The movement of the needle 1510 disconnects connective tissue 1512 to allow "relaxation" of the skin and create a smoother appearance of the skin 1504. PRP and PPP can be applied to the treated area by any means. One method is to apply PPP, PRP and an activator, with no limitation to the order of application, on top of treated section of skin 1504 during the treatment. Another method is to apply PPP, PRP and an activator, with no limitation to the order of application, to the section of skin 1504 through the needle 1510 after treatment with the needle. The PRP can be also applied inside the treated area 1504 while the needle 1508 disconnects the connective tissue 1512; afterwards, the PPP can be applied with the activator on the surface of the skin 1504 to seal the wound caused by the needle 1510 insertion. Other variations may be applied.

Figure 15B:
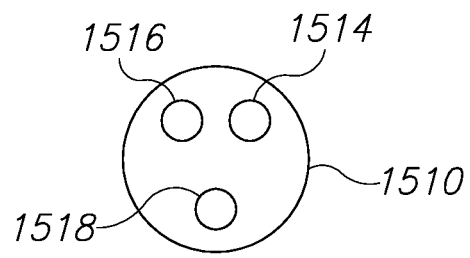
Figure 15C:
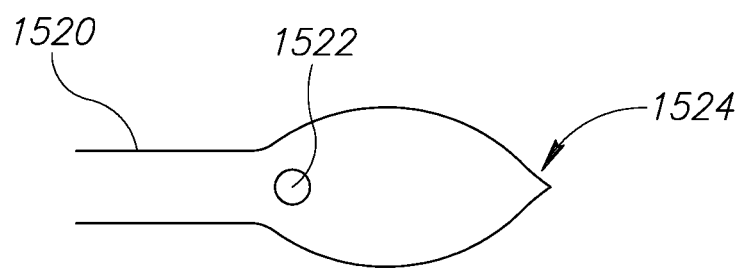
Figure 15D:
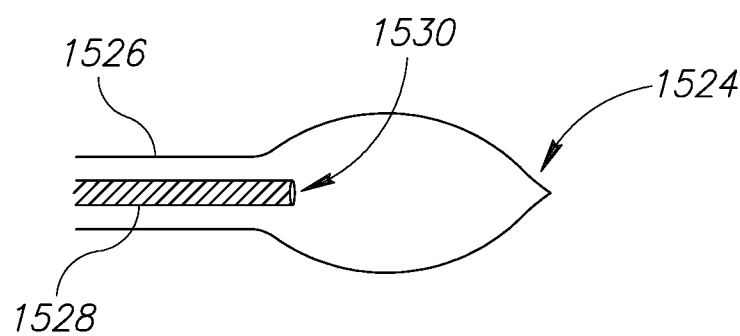

The needle 1510 is further illustrated in different embodiments in FIG. 15C and FIG. 15D. FIG. 15C shows a hollowed shaft 1520 that has an opening 1522 next to a blade 1524. While or after the blade 1524 disconnects connective tissue 1512, the PRP, PPP and activator can be applied through opening 1522.

FIG. 15D shows another embodiment of the needle 1510. One shaft 1526 and one hollowed lumen 1528 are connected to each other in parallel. The shaft 1526 ends with a blade 1524 that is used to disconnect the connective tissue 1512. The hollowed lumen 1528 may be used to apply PRP, PPP and activator through aperture 1530 to the skin 1504 during the disconnection of the connective tissue 1512 or after the treatment for enhancing wound healing.

FIG. 15B shows a front view of the aperture 1522 or 1530 in the tip of the needle 1510. The aperture 1522 or 1530 may be also configure to include a number of lumens, for example, at least one nozzle for dispensing PRP 1514, at least one nozzle for dispensing PPP 1516 and at least one nozzle for dispensing activator 1518. The respective aperture 1522 or 1530 may apply the above materials while the needle 1510 is moving in x-y directions 1507 within skin section 1504.

Example 1

Three ml of blood were withdrawn using a syringe as described in the present application and shown in FIGS. 1A and 1B from the patient and were mixed with Heparin to prevent coagulation. The platelets count in the whole blood was found to be $326 \times 10^3$ in $mm^3$. The syringe was then capped and centrifuged for 12 minutes at 1000 RPM (Rotofix 32a with 15 ml tubes adaptor, Hettich, Germany). After centrifugation the blood and plasma were found to have separated in the syringe with the red blood cells layer having been moved to under the plasma layer. The plasma was then transferred to the inner chamber 106 of the syringe as described herein. Once the inner chamber's content were separated from the barrel's content, the red blood cells layer were discarded by uncapping the barrel and pushing the red blood cells out of the syringe using the piston. The syringe was then capped and the plasma layer contents moved to the main chamber as described herein. After centrifugation, the platelets count was found to be $523 \times 10^3$ in $mm^3$ in the plasma layer. A second centrifugation was performed at 2500 RPM for 2 minutes. After centrifugation, the content were found to have separated into a viscous layer at the bottom of the barrel and a liquid layer above that layer. The liquid layer was moved to the secondary chamber in the same manner as described above. The platelet count for the contents in the main chamber was measured to be $1364 \times 10^3$ in $mm^3$. Thus, the platelet count using the syringe apparatus of the present invention and the centrifugation process described above increased from $326 \times 10^3$ in $mm^3$ $1364 \times 10^3$ in $mm^3$, a more than four folds increase.

What is claimed is:

1. A dual chambered syringe comprising:
   (a) a hollow inner barrel having an open proximal end, a distal end, and defining a first inner chamber, wherein the inner barrel comprises a screw thread on its exterior surface;
   (b) a hollow outer barrel concentric with the hollow inner barrel, the outer barrel having a proximal end, a distal end, and defining a second inner chamber;
      wherein the inner barrel distal end is adapted to be inserted into the outer barrel proximal end; and
      wherein the outer barrel distal end is adapted for receiving fluids into and dispensing fluids from the second inner chamber;
   (c) a tooth positioned to engage the screw thread when the inner barrel is inserted into the second inner chamber;
   (d) an apertured stopper positioned at the inner barrel distal end and providing a fluid flow path between the first inner chamber and the second inner chamber; and
   (e) a moveable shaft positioned within the inner chamber through the inner barrel open proximal end and adapted to reversibly seal the aperture of the stopper.

2. The dual chambered syringe of claim 1, wherein the tooth may be selectively engaged or disengaged from the screw thread.

3. The dual chambered syringe of claim 1, wherein the aperture and the shaft distal end comprise screw thread pair members.

4. The dual chambered syringe of claim 1, wherein the outer barrel distal end comprises a Luer lock.

5. The dual chambered syringe of claim 1, wherein the dual chambered syringe further comprises a dispensing apparatus attached to the outer barrel distal end.

6. The dual chambered syringe of claim 5, wherein the dispensing apparatus comprises a multineedle device comprising a plurality of hollow needles.

7. The dual chambered syringe of claim 6, wherein the needles are parallel to one another.

8. The dual chambered syringe of claim 6, wherein the needles are fixed to a roller delivery system, the roller delivery system having an axis perpendicular to the longitudinal axis of the syringe and wherein the second inner chamber is in fluid communication with the roller delivery system and the roller delivery system is in fluid communication with the hollow needles.

9. The dual chambered syringe of claim 1, further comprising a laser source and a controller, wherein the controller is configured to first cause ablation of one or more microchannels in a skin tissue surface and then to cause a dispenser to dispense fluid from the distal end of the syringe into the microchannels and on to the skin tissue surface.

10. The dual chambered syringe of claim 9, wherein the fluid dispensed is platelet-rich plasma or platelet-poor plasma.

11. A cosmetic method of dispensing fluids in connection with a laser fractional cosmetic skin tissue treatment comprising:
   providing the dual chamber syringe of claim 1;
   causing a laser to create one or more microchannels in the skin tissue; and,
   dispensing a first fluid from the distal end of the syringe onto the skin tissue surface.

12. The method of claim 11, further comprising dispensing a second fluid onto the skin tissue surface.

13. The method of claim 12, wherein the first fluid comprises platelet-rich plasma (PRP) and wherein the second fluid comprises platelet-poor plasma (PPP).

14. The method of claim 13, wherein the PRP and the PPP are dispensed from the same dual chamber syringe.

15. The method of claim 12, wherein the dispensed fluids are sprayed into the microchannels and onto the skin tissue surface by air pressure.

16. A method of preparing platelet-rich plasma (PRP) or platelet-poor plasma (PPP) or both comprising:
   (a) providing the dual chamber syringe of claim 1;
   (b) providing a volume of whole blood to the second inner chamber of the syringe;
   (c) centrifuging the syringe so that red blood cells are separated from platelets;
   (d) moving the platelets into the first inner chamber by opening the apertured stopper and moving the inner barrel in the direction of the distal end of the outer barrel until the platelets are contained in the first inner chamber;
   (e) closing the apertured stopper;
   (f) removing the red blood cells from the syringe through the distal end of the second inner chamber;
   (g) moving the platelets from the first inner chamber to the second inner chamber by opening the apertured stopper and moving the inner barrel in a direction away from the distal end of the outer chamber; and,
   (h) dispensing the platelets.

17. The method of claim 16, further comprising, after step (g):
   (i) centrifuging the syringe to separate the PRP from the PPP;
   (j) moving the PPP from the second inner chamber to the first inner chamber through the apertured stopper;
   (k) dispensing PRP in the second inner chamber.

18. The method of claim 17, further comprising:
   (l) moving the PPP from the first inner chamber to the second inner chamber by opening the apertured stopper; and,
   (m) dispensing the PPP.

19. A cosmetic method comprising:
   providing the dual chamber syringe of claim 1;
   create one or more microchannels in the skin tissue using a multineedle device; and,
   dispensing a first fluid from the distal end of the syringe into the formed microchannels.

20. The method of claim 19, further comprising dispensing a second fluid into the formed microchannels.

21. The method of claim 20, wherein the first fluid comprises platelet-rich plasma (PRP) and wherein the second fluid comprises platelet-poor plasma (PPP).

22. The method of claim 21, wherein the PRP and the PPP are dispensed from the same dual chamber syringe.

* * * * *